(12) United States Patent
Li et al.

(10) Patent No.: US 7,771,755 B2
(45) Date of Patent: Aug. 10, 2010

(54) INJECTABLE CALCIUM PHOSPHATE SOLID RODS AND PASTES FOR DELIVERY OF OSTEOGENIC PROTEINS

(75) Inventors: Rebecca Li, Bedford, MA (US); Howard Seeherman, Cambridge, MA (US); Hyun Kim, Bedford, MA (US)

(73) Assignees: Wyeth, Madison, NJ (US); Etex Corporation, Cambridge, MA (US)

( * ) Notice: Subject to any disclaimer, the term of this patent is extended or adjusted under 35 U.S.C. 154(b) by 1216 days.

(21) Appl. No.: 10/937,364

(22) Filed: Sep. 10, 2004

(65) Prior Publication Data

US 2005/0089579 A1 Apr. 28, 2005

Related U.S. Application Data

(60) Provisional application No. 60/502,493, filed on Sep. 12, 2003.

(51) Int. Cl.
*A61K 38/23* (2006.01)
*A61K 33/42* (2006.01)

(52) U.S. Cl. .................. 424/602; 424/499; 514/12; 530/350

(58) Field of Classification Search ................ 424/602, 424/499; 514/12; 530/350
See application file for complete search history.

(56) References Cited

U.S. PATENT DOCUMENTS

| | | | |
|---|---|---|---|
| 2,465,357 A | 3/1949 | Correll et al. | |
| 3,955,719 A | 5/1976 | Pheulpin | |
| 4,191,747 A | 3/1980 | Scheicher | |
| 4,294,753 A | 10/1981 | Urist | |
| 4,394,370 A | 7/1983 | Jeffries | |
| 4,399,216 A | 8/1983 | Axel et al. | |
| 4,419,446 A | 12/1983 | Howley et al. | |
| 4,434,094 A | 2/1984 | Seyedin et al. | |
| 4,441,915 A | 4/1984 | Arndt et al. | |
| 4,455,256 A | 6/1984 | Urist | |
| 4,468,464 A | 8/1984 | Cohen et al. | |
| 4,472,840 A | 9/1984 | Jefferies | |
| 4,553,542 A | 11/1985 | Schenk et al. | |
| 4,563,350 A | 1/1986 | Nathan et al. | |
| 4,596,574 A | 6/1986 | Urist | |
| 4,608,199 A | 8/1986 | Caplan et al. | |
| 4,619,989 A | 10/1986 | Urist | |
| 4,627,982 A | 12/1986 | Seyedin et al. | |
| 4,642,120 A | 2/1987 | Nevo et al. | |
| 4,662,884 A | 5/1987 | Stenaas | |
| 4,681,763 A | 7/1987 | Nathanson | |
| 4,703,008 A | 10/1987 | Lin | |
| 4,727,028 A | 2/1988 | Santerre et al. | |
| 4,737,578 A | 4/1988 | Evans | |
| 4,758,233 A | 7/1988 | Phillips et al. | |
| 4,761,471 A | 8/1988 | Urist | |
| 4,766,067 A | 8/1988 | Biswas et al. | |
| 4,767,628 A | 8/1988 | Hutchinson | |
| 4,769,328 A | 9/1988 | Murray et al. | |
| 4,774,228 A | 9/1988 | Seyedin et al. | |
| 4,774,322 A | 9/1988 | Seyedin et al. | |
| 4,784,055 A | 11/1988 | Langen et al. | |
| 4,789,732 A | 12/1988 | Urist | |
| 4,795,804 A | 1/1989 | Urist | |
| 4,798,885 A | 1/1989 | Mason | |
| 4,804,744 A | 2/1989 | Sen | |
| 4,810,691 A | 3/1989 | Seyedin | |
| 4,828,990 A | 5/1989 | Higashi et al. | |
| 4,843,063 A | 6/1989 | Seyedin | |
| 4,851,521 A | 7/1989 | Della Valle et al. | |
| 4,868,161 A | 9/1989 | Roberts | |
| 4,877,864 A | 10/1989 | Wang et al. | |
| 4,886,747 A | 12/1989 | Derynck | |
| 4,908,204 A | 3/1990 | Robinson et al. | |
| 4,920,962 A | 5/1990 | Proulx | |
| 4,923,805 A | 5/1990 | Reddy et al. | |
| 4,955,892 A | 9/1990 | Daniloff et al. | |
| 4,963,146 A | 10/1990 | Li | |
| 4,968,590 A | 11/1990 | Kuberasampath et al. | |
| 4,992,274 A | 2/1991 | Robinson et al. | |
| 5,011,486 A | 4/1991 | Aebischer et al. | |
| 5,011,691 A | 4/1991 | Oppermann | |
| 5,013,649 A | 5/1991 | Wang et al. | |
| 5,019,087 A | 5/1991 | Nichols | |
| 5,024,841 A | 6/1991 | Chu et al. | |

(Continued)

FOREIGN PATENT DOCUMENTS

EP 0 052 510 5/1982

(Continued)

OTHER PUBLICATIONS

Aldrich Handbook of Fine Chemicals and Laboratory Equipment, Syringe section, p. T679 (2000-2001).*

(Continued)

*Primary Examiner*—Chih-Min Kam
(74) *Attorney, Agent, or Firm*—Finnegan, Henderson, Farabow, Garrett & Dunner, L.L.P.

(57) ABSTRACT

Osteogenic proteins are delivered via an injectable solid rod or hardenable paste. The formulation comprises a calcium phosphate material, an osteogenic protein, and optional additives and active ingredients such as a bone resorption inhibitor. Methods of making injectable pharmaceutical compositions and methods of using the osteogenic compositions to treat bone defects are also disclosed.

29 Claims, 2 Drawing Sheets

U.S. PATENT DOCUMENTS

| | | |
|---|---|---|
| 5,026,381 A | 6/1991 | Li |
| 5,041,538 A | 8/1991 | Ling et al. |
| 5,071,834 A | 12/1991 | Burton et al. |
| 5,089,396 A | 2/1992 | Mason et al. |
| 5,102,807 A | 4/1992 | Burger et al. |
| 5,106,626 A | 4/1992 | Parsons et al. |
| 5,106,748 A | 4/1992 | Wozney et al. |
| 5,108,753 A | 4/1992 | Kuberasampath |
| 5,108,922 A | 4/1992 | Wang et al. |
| 5,116,738 A | 5/1992 | Wang et al. |
| 5,118,667 A | 6/1992 | Adams et al. |
| 5,124,316 A | 6/1992 | Antoniades et al. |
| 5,141,905 A | 8/1992 | Rosen et al. |
| 5,147,399 A | 9/1992 | Dellon et al. |
| 5,166,058 A | 11/1992 | Wang et al. |
| 5,166,190 A | 11/1992 | Mather et al. |
| 5,166,322 A | 11/1992 | Shaw et al. |
| 5,168,050 A | 12/1992 | Hammonds |
| 5,171,579 A | 12/1992 | Ron et al. |
| 5,187,076 A | 2/1993 | Wozney et al. |
| 5,187,263 A | 2/1993 | Murray et al. |
| 5,202,120 A | 4/1993 | Silver et al. |
| 5,206,028 A | 4/1993 | Li |
| 5,208,219 A | 5/1993 | Ogawa et al. |
| 5,215,893 A | 6/1993 | Mason et al. |
| 5,216,126 A | 6/1993 | Cox et al. |
| 5,217,867 A | 6/1993 | Evans et al. |
| 5,218,090 A | 6/1993 | Connors |
| 5,229,495 A | 7/1993 | Ichijo et al. |
| 5,256,418 A | 10/1993 | Kemp et al. |
| 5,258,494 A | 11/1993 | Oppermann et al. |
| 5,266,683 A | 11/1993 | Oppermann et al. |
| 5,278,145 A | 1/1994 | Keller et al. |
| 5,284,756 A | 2/1994 | Grinna et al. |
| 5,286,654 A | 2/1994 | Cox et al. |
| 5,290,271 A | 3/1994 | Jernberg |
| 5,292,802 A | 3/1994 | Rhee et al. |
| 5,306,307 A | 4/1994 | Senter et al. |
| 5,308,889 A | 5/1994 | Rhee et al. |
| 5,324,519 A | 6/1994 | Dunn et al. |
| 5,324,775 A | 6/1994 | Rhee et al. |
| 5,328,955 A | 7/1994 | Rhee et al. |
| 5,352,715 A | 10/1994 | McMullin et al. |
| 5,354,557 A | 10/1994 | Oppermann et al. |
| 5,356,629 A | 10/1994 | Sander et al. |
| 5,364,839 A | 11/1994 | Gerhart et al. |
| 5,366,875 A | 11/1994 | Wozney et al. |
| 5,399,346 A | 3/1995 | Anderson et al. |
| 5,399,677 A | 3/1995 | Wolfman et al. |
| 5,405,390 A | 4/1995 | O'Leary et al. |
| 5,411,941 A | 5/1995 | Grinna et al. |
| 5,413,989 A | 5/1995 | Ogawa et al. |
| 5,420,243 A | 5/1995 | Ogawa et al. |
| 5,422,340 A | 6/1995 | Ammann et al. |
| 5,447,725 A | 9/1995 | Damiani et al. |
| 5,455,041 A | 10/1995 | Genco et al. |
| 5,455,329 A | 10/1995 | Wingender |
| 5,457,047 A | 10/1995 | Wingender |
| 5,457,092 A | 10/1995 | Schulter |
| 5,459,047 A | 10/1995 | Wozney et al. |
| 5,464,440 A | 11/1995 | Johannsson |
| 5,508,263 A | 4/1996 | Grinna et al. |
| 5,516,654 A | 5/1996 | Israel |
| 5,520,923 A | 5/1996 | Tjia et al. |
| 5,538,892 A | 7/1996 | Donahoe et al. |
| 5,543,394 A | 8/1996 | Wozney et al. |
| 5,545,616 A | 8/1996 | Woddruff |
| 5,547,854 A | 8/1996 | Donahoe et al. |
| 5,556,767 A | 9/1996 | Rosen et al. |
| 5,618,924 A | 4/1997 | Wang et al. |
| 5,631,142 A | 5/1997 | Wang et al. |
| 5,635,372 A | 6/1997 | Celeste et al. |
| 5,635,373 A | 6/1997 | Wozney et al. |
| 5,637,480 A | 6/1997 | Celeste et al. |
| 5,639,638 A | 6/1997 | Wozney et al. |
| 5,645,592 A | 7/1997 | Nicolais et al. |
| 5,648,467 A | 7/1997 | Kobayashi et al. |
| 5,650,176 A | 7/1997 | Lee et al. |
| 5,650,494 A | 7/1997 | Cerletti et al. |
| 5,658,882 A | 8/1997 | Celeste et al. |
| 5,661,007 A | 8/1997 | Wozney et al. |
| 5,674,292 A * | 10/1997 | Tucker et al. ............... 424/422 |
| 5,676,976 A | 10/1997 | Lee et al. |
| 5,688,678 A | 11/1997 | Hewick et al. |
| 5,693,779 A | 12/1997 | Moos, Jr. et al. |
| 5,700,664 A | 12/1997 | Bennett |
| 5,700,774 A | 12/1997 | Hattersley et al. |
| 5,700,911 A | 12/1997 | Wozney et al. |
| 5,703,043 A | 12/1997 | Celeste et al. |
| 5,728,679 A | 3/1998 | Celeste et al. |
| 5,750,651 A | 5/1998 | Oppermann et al. |
| 5,752,974 A | 5/1998 | Rhee et al. |
| 5,756,457 A | 5/1998 | Wang et al. |
| 5,786,217 A | 7/1998 | Tubo et al. |
| 5,813,411 A | 9/1998 | Van Bladel et al. |
| 5,827,733 A | 10/1998 | Lee et al. |
| 5,846,931 A | 12/1998 | Hattersley et al. |
| 5,849,880 A | 12/1998 | Wozney et al. |
| 5,866,364 A | 2/1999 | Israel et al. |
| 5,932,216 A | 8/1999 | Celeste et al. |
| 5,935,594 A | 8/1999 | Ringeisen et al. |
| 5,936,067 A | 8/1999 | Graham et al. |
| 5,939,323 A | 8/1999 | Valentini et al. |
| 5,939,388 A | 8/1999 | Rosen et al. |
| 5,965,403 A | 10/1999 | Celeste et al. |
| 5,972,368 A | 10/1999 | MacKay |
| 5,986,058 A | 11/1999 | Lee et al. |
| 6,001,352 A | 12/1999 | Boyan et al. |
| 6,004,937 A | 12/1999 | Wood et al. |
| 6,015,801 A | 1/2000 | Daifotis et al. |
| 6,027,919 A | 2/2000 | Celeste et al. |
| 6,034,061 A | 3/2000 | Rosen et al. |
| 6,034,062 A | 3/2000 | Thies et al. |
| 6,132,214 A | 10/2000 | Sohonen et al. |
| 6,150,328 A | 11/2000 | Wang et al. |
| 6,177,406 B1 | 1/2001 | Wang et al. |
| 6,187,742 B1 | 2/2001 | Wozney et al. |
| 6,190,880 B1 | 2/2001 | Israel et al. |
| 6,207,813 B1 | 3/2001 | Wozney et al. |
| 6,221,958 B1 | 4/2001 | Shalaby et al. |
| 6,245,889 B1 | 6/2001 | Wang et al. |
| 6,284,872 B1 | 9/2001 | Celeste et al. |
| 6,287,816 B1 | 9/2001 | Rosen et al. |
| 6,291,206 B1 | 9/2001 | Wozney et al. |
| 6,331,612 B1 | 12/2001 | Celeste et al. |
| 6,340,668 B1 | 1/2002 | Celeste et al. |
| 6,432,919 B1 | 8/2002 | Wang et al. |
| 6,437,111 B1 | 8/2002 | Wozney et al. |
| 6,558,925 B2 | 5/2003 | Graham et al. |
| 6,586,388 B2 | 7/2003 | Oppermann et al. |
| 6,593,109 B1 | 7/2003 | Israel et al. |
| 6,610,513 B2 | 8/2003 | Wozney et al. |
| 6,613,744 B2 | 9/2003 | Wozney et al. |
| 6,623,934 B2 | 9/2003 | Celeste et al. |
| 6,699,471 B2 | 3/2004 | Radici et al. |
| 6,719,968 B2 | 4/2004 | Celeste et al. |
| 2002/0187104 A1* | 12/2002 | Li et al. ..................... 424/44 |

FOREIGN PATENT DOCUMENTS

| | | |
|---|---|---|
| EP | 0 058 481 | 8/1982 |
| EP | 0 121 976 | 10/1984 |
| EP | 0 128 041 | 12/1984 |
| EP | 0 148 155 | 7/1985 |

| | | |
|---|---|---|
| EP | 0 155 476 | 9/1985 |
| EP | 0 169 016 | 1/1986 |
| EP | 0 177 343 | 4/1986 |
| EP | 0 222 491 | 10/1986 |
| EP | 0 212 474 | 3/1987 |
| EP | 0 241 809 | 10/1987 |
| EP | 0 336 760 | 4/1989 |
| EP | 0 329 239 | 8/1989 |
| EP | 0 394 418 | 10/1990 |
| EP | 0 401 055 | 12/1990 |
| EP | 0 409 472 | 1/1991 |
| EP | 0 416 578 | 3/1991 |
| EP | 0 429 570 | 6/1991 |
| EP | 0 433 225 | 6/1991 |
| EP | 0 512 844 | 11/1992 |
| EP | 0 530 804 | 3/1993 |
| EP | 0 531 448 | 11/1994 |
| EP | 0 626 451 | 11/1994 |
| EP | 0 688 869 | 12/1995 |
| EP | 0 831 884 | 5/1996 |
| EP | 0 313 578 | 8/1996 |
| EP | 0 741 187 | 11/1996 |
| EP | 0 592 562 | 1/1999 |
| EP | 1 061 940 | 2/1999 |
| EP | 0 536 186 | 11/2001 |
| JP | 63-181770 A | 7/1988 |
| JP | 05-123390 A2 | 5/1993 |
| JP | 03-345189 | 7/1993 |
| JP | 05-277174 A2 | 10/1993 |
| JP | 2000-202024 | 7/2000 |
| WO | WO 84/01106 | 3/1984 |
| WO | WO 85/04173 | 9/1985 |
| WO | WO 86/00525 | 1/1986 |
| WO | WO 86/00639 | 1/1986 |
| WO | WO 87/00528 | 1/1987 |
| WO | WO 88/00205 | 1/1988 |
| WO | WO 89/09787 | 10/1989 |
| WO | WO 89/09788 | 10/1989 |
| WO | WO 89/10133 | 11/1989 |
| WO | WO 89/10409 | 11/1989 |
| WO | WO 90/03733 | 4/1990 |
| WO | WO 90/11366 | 10/1990 |
| WO | WO 91/02744 | 3/1991 |
| WO | WO 91/04274 | 4/1991 |
| WO | WO 91/05802 | 5/1991 |
| WO | WO 91/10444 | 7/1991 |
| WO | WO 91/17777 | 11/1991 |
| WO | WO 91/18047 | 11/1991 |
| WO | WO 91/18098 | 11/1991 |
| WO | WO 92/05198 | 4/1992 |
| WO | WO 92/05199 | 4/1992 |
| WO | WO 92/07004 | 4/1992 |
| WO | WO 92/07073 | 4/1992 |
| WO | WO 92/14481 | 9/1992 |
| WO | WO 92/15323 | 9/1992 |
| WO | WO 92/09697 | 11/1992 |
| WO | WO 92/20793 | 11/1992 |
| WO | WO 92/22319 | 12/1992 |
| WO | WO 93/00049 | 1/1993 |
| WO | WO 93/00050 | 1/1993 |
| WO | WO 93/00432 | 1/1993 |
| WO | WO 93/04692 | 3/1993 |
| WO | WO 93/05751 | 4/1993 |
| WO | WO 93/06872 | 4/1993 |
| WO | WO 93/09228 | 5/1993 |
| WO | WO 93/09229 | 5/1993 |
| WO | WO 93/09802 | 5/1993 |
| WO | WO 93/13206 | 7/1993 |
| WO | WO 93/16099 | 8/1993 |
| WO | WO 93/19177 | 9/1993 |
| WO | WO 93/20858 | 10/1993 |
| WO | WO 94/01557 | 1/1994 |
| WO | WO 94/03200 | 2/1994 |
| WO | WO 94/06449 | 3/1994 |
| WO | WO 94/11502 | 5/1994 |
| WO | WO 94/15949 | 7/1994 |
| WO | WO 94/15965 | 7/1994 |
| WO | WO 94/15966 | 7/1994 |
| WO | WO 94/21681 | 9/1994 |
| WO | WO 94/24285 | 10/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/05846 | 3/1995 |
| WO | WO 95/07982 | 3/1995 |
| WO | WO 95/10539 | 4/1995 |
| WO | WO 95/10611 | 4/1995 |
| WO | WO 95/12664 | 5/1995 |
| WO | WO 95/15966 | 6/1995 |
| WO | WO 95/16035 | 6/1995 |
| WO | WO 95/33830 | 12/1995 |
| WO | WO 96/01845 | 1/1996 |
| WO | WO 96/02559 | 2/1996 |
| WO | WO 96/36710 | 11/1996 |
| WO | WO 96/38570 | 12/1996 |
| WO | WO 96/39170 | 12/1996 |
| WO | WO 96/39203 | 12/1996 |
| WO | WO 96/40883 | 12/1996 |
| WO | WO 97/15321 | 5/1997 |
| WO | WO 97/22308 | 6/1997 |
| WO | WO 97/34626 | 9/1997 |
| WO | WO 97/40137 | 10/1997 |
| WO | WO 97/45532 | 12/1997 |
| WO | WO 97/48275 | 12/1997 |
| WO | WO 97/49412 | 12/1997 |
| WO | WO 98/16641 | 4/1998 |
| WO | WO 98/31788 | 7/1998 |
| WO | WO 98/34951 | 8/1998 |
| WO | WO 98/40113 | 9/1998 |
| WO | WO 98/49296 | 11/1998 |
| WO | WO 99/01159 | 1/1999 |
| WO | WO 99/24070 | 5/1999 |
| WO | WO 99/31120 | 6/1999 |
| WO | WO 99/37320 | 7/1999 |
| WO | WO 99/38543 | 8/1999 |
| WO | WO 99/45949 | 9/1999 |
| WO | WO 00/37124 | 6/2000 |
| WO | WO 00/43781 A | 7/2000 |
| WO | WO 00/47117 | 8/2000 |
| WO | WO 01/28602 | 4/2001 |
| WO | WO 01/28603 | 4/2001 |
| WO | WO 02/100331 | 12/2002 |
| WO | WO 03/099992 | 12/2003 |

OTHER PUBLICATIONS

Hollinger et al., *Trans. Res. Orthop. Soc.* 22, 189 (1999).*
Seeherman et al., *J. Bone and Joint Surgery* 88, 1553-1565 (2006).*
Aiba et al., *Blood*, 90:3923-3030 (1997).
Alberts et al., *Molecular Biology of the Cell, Third Ed.*, Garland Publishing, Inc., New York, NY, pp. 1142 (1983).
Amizuka et al., *J. Cell Biol.*, 126:1611-1623 (1994).
Attisano et al., *Cell*, 68:97-108 (1992).
Baird et al., *Biochem. Biophys. Res. Comm.*, 138:476-482 (1986).
Barres. B.A. et al., *Development*, 118:283-295 (1993).
Basler, K. et al., *Cell*, 73:687-702 (1993).
Beck et al., *Growth Factors*, 2:273-282 (1990).
Belo et al., *Mech. Devel.*, 68:45-57 (1997).
Bendig, *Genetic Engineering*, 7:91-127 (1988).
Biben et al., *Develop. Biol.*, 194:135-151 (1998).
Bignami et al., *Brain Res.*, 43:429-435 (1972).
Bignami, A. et al., *Plasticity and Regeneration of the Nervous System*, 197-206 (1991).
Bolton et al., *Biochem J.*, 133:529 (1973).
Border et al., *J. Clin. Invest.*, 90:1-7 (1992).

Bouwmeester et al., *Nature*, 382:595-601 (1996).
Bowen-Pope et al., *J. Biol. Chem.*; 237:5161 (1982).
Bowie et al., *Science*, 247:1306-1310 (1990).
Brown et al., *J. Immunol.*, 142:679 (1989).
Broxmeyer et al., *PNAS*, 85:9052 (1988).
Bruder et al., *J. Cell Biochem.*, 56:283-294 (1994).
Burt, D.W., *BBRC*, 184:590-595 (1992).
Campoccia et al., *Biomaterials*, 19:2101-27 (1998).
Caplan, A., *Bone Repair and Regeneration*, 21:429-435 (1994).
Celeste et al., *J. Bone Mineral Res.*, 9:suppl. 5136 (1994).
Celeste et al., *PNAS*, 87:9843-9847 (1990).
Chang et al., *J. Biol. Chem.*, 269:28227-28234 (1994).
Conlon et al., *Development*, 120:1919 (1994).
Conlon et al., *Development*, 111:969 (1991).
Collignon et al., *Nature*, 381:155 (1996).
Creighton, T.E., *Proteins: Structure and Molecular Principles*, W.H. Freeman and Co., New York (1983).
Cunningham et al., *PNAS*, 89:11740-11744 (1992).
Dagert et al., *Gene*, 6:23 (1979).
Dale et al., *EMBO J.*, 12:4471 (1993).
D'Alessandro et al., *Growth Factors*, 11:53-69 (1994).
D'Allesandro et al., *J. Bone Mineral Res.*, (6) Suppl: 1:S153 (1991).
DeWulf et al., *Endocrinology*, 136:2652-2663 (1995).
Dexter et al., *Nature*, 344:380 (1990).
DiLeone et al., *Genetics*, 148:401-408 (1998).
Doctor et al., *Dev. Biol.*, 151:591-605 (1992).
Ducy et al., *Kidney Intl.*, 57:2207-2214 (2000).
Dunn et al., *Cancer Cells*, 3:227-234 (1985).
Ebner et al., *Science*, 260:1344-1348 (1993).
Estevez et al., *Nature*, 365:644-649 (1993).
Eto et al., *Biochem. Biophys. Res. Comm.*, 142:1095 (1987).
Fainsod et al., *Mech. Dev.*, 1:39-50 (1997).
Fallon et al., *J. Cell Biol.*, 100:198-207 (1985).
Fenton et al., *Endocrinology*, 129:1762-1768 (1991).
Finch et al., *PNAS*, 94:6770-6775 (1997).
Frishchauf et al., *J. Mol. Biol.*, 170:827-842 (1983).
Frommel et al., *J. Mol. Evol.*, 24:233-257 (1985).
Gamer et al., *Develop. Biol.*, 208:222-232 (1999).
Geisert et al., *Develop. Biol.*, 143:335-345 (1991).
Gerhart et al., *Trans. Othop. Res. Soc.*, 16:172 (1991).
Gething et al., *Nature*, 293:620-625 (1981).
Gitelman et al., *J. Cell. Biol.*,126:1595-1609 (1994).
Goodman, R., *Methods for Serum-Free Culture of Neuronal and Lymphoid Cells*, 23-36 (1984).
Gough et al., *EMBO J.*, 4:645-653 (1985).
Graham et al., *EMBO*, 15:6505-6515 (1996).
Graham et al., *Growth Factors*, 7:151-160 (1992).
Graham et al., *J. Biol. Chem.*, 269:4974-4978 (1994).
Graham et al., *Nature*, 344:442 (1990).
Guigon et al., *Chem. Abstracts*, 96:36, Abstract No. 115633h (1982).
Guigon et al., *Cancer Res.*, 42:638 (1982).
Hammonds et al., *Mol. Endocrin.*, 5:149-155 (1991).
Harrison et al., *Exp. Cell Res.*, 92:340-345 (1991).
Hasimoto et al., *J. Biol. Chem.*, 267:7203-7206 (1992).
He et al., *Develop. Dynamics*, 196:133-142 (1993).
Hebda et al., *J. Invest. Dermatol.*, 91:440-445 (1988).
Hefti et al., *J. Neurobiol.*, 25:1418-1435 (1994).
Hemmati-Brinvanlou et al., *Nature*, 359:609-614 (1992).
Hoang et al., *J. Biol. Chem.*, 271:26131-26137 (1996).
Hollnagel et al., *Calcified Tissue Int'l*, 56:430 (1995).
Hunkapiller et al., *Meth. Enzymol.*, 91:399-413 (1983).
Inouye et al., *Mol. Cell. Endocrinol.*, 90:1 (1992).
Iwasaki, *J. Biol. Chem.*, 271:17360-5 (1996).
Janowska-Wieczorek et al., *Biol. Abstracts, Reviews-Reports-Meetings*, 33:61402 (1987).
Jonhagen et al., *Dement. Cogn. Disord.*, 9:246-257 (1998).
Joyce et al, *J. Cell Biochem.*, Suppl.17E:136, Abstract R504 (1993).
Kalyani et al., *J. Neuroscience*, 18:7856-7869 (1998).
Karaplis et al., *Mol. Endocrin.*, 4:441-446 (1990).
Karaplis et al., *Genes & Development*, 8:277-289 (1994).
Katagiri et al., *J. Cell Biol.*, 127:1755-1766 (1994).
Kaufman et al., *Mol. Cell Biol.*, 2:1304-1319 (1982).
Kaufman et al., *Mol. Cell Biol.*, 5:1750-1759 (1985).
Kaufman et al., *J. Mol. Biol.*, 159:601-629 (1982).
Kaufman et al., *PNAS*, 82:689-693 (1985).
Kingsley et al., *Cell*, 71:399-410 (1992).
Kingsley et al., *Genes & Development*, 8:133-146 (1994).
Klein-Nulend et al., *Tissue Engineering*, 4:305-313 (1998).
Klein et al., *Brain Res.* 875:144-151 (2000).
Kliot et al., *Exper. Neur.*, 109:57-69 (1990).
Koenig et al., *Mol. Cell Biol.*, 14:5961-5974 (1994).
Koopman et al., *JBC*, 273:10103-10109 (1997).
Krueger, G.G., , *N. E. J. Med.*, 328:1845-1846 (1993).
LaPan et al., Program and Abstract, 13th Ann. Mtg of the AM Society of Bone and Min. Res., 8/24-28, p. 5153, Abstract No. 280, Mary Ann Liebert, Inc. NY (1991).
Lathe, J., *J. Mol. Biol.*, 183:1-12 (1985).
Lawn et al., *Cell*, 15:1157-1174 (1978).
Lefer et al., *PNAS*, 90:1018-22 (1993.
LeMaire et al., *Trends in Genetics*, 12:525-531 (1996).
Leslie M., *Nurse Practitioner*, 24:38, 41-8 (1999).
Lewin, *Science*, 237:1570 (1987).
Leyns et al., *Cell*, 88:747-756 (1997).
Lin et al., *Cell*, 68:775-785 (1992).
Lin et al., *Science*, 260:1130-1132 (1993).
Lipes et al., *PNAS*, 85:9704 (1988).
Lodish et al., *Mol. Cell Biol.*, 3rd Ed., W.H. Freeman & Co., p. 266 (1995).
Lopez-Coviella et al., *J. Physiol. Paris.*, 92:460-461 (1998).
Lopez-Coviella et al., *Science*, 289:313-316 (2000).
Lopez-Coviella et al., *Xth International Symposium on Cholinergic Mechanisms* (1998).
Lopez-Coviella et al., *Soc. Neurosci. Abstracts*, 25:517 (1999).
Lord et al., *Brit. J. Haematol.*, 34:441 (1976).
Lorimore et al., *Leuk. Res.*, 14:481-489 (1990).
Lowe et al., *Nature*, 381:158 (1996).
Lucas et al., *Differentiation*, 37:47-52 (1988).
Luthman et al., *Nucl. Acids Res.*, 11:1295-1308 (1983).
Luyten et al., *J. Biol. Chem.*, 264:13377-13380 (1989).
Luyten et al., *Exp. Cell. Res.*, 210(2):224-229 (1994).
Lyons et al., *PNAS*, 86:4554-4558 (1989).
Mangin et al., *PNAS*, 85:597-601 (1988).
Mangin et al., Gene, 95:195-202 (1990).
Maniatis et al., *Mol. Cloning, A Laboratory Manual, Cold Spring Harbor Laboratory*, CSH., N.Y.:310-323, 387-389 & 404-433 (1982).
Mantel et al., *PNAS*, 90:2232-2236 (1993).
Mansour et al., *J. Neurosci. Res.*, 25:300-377 (1990).
Marieb, E.N., *In Human Anatomy and Physiology*, 2nd Ed., The Benjamin/Cummings Publishing Co., pp. 373-375 (1992).
Mark, *J. Cell. Biol.*, 130:701-10 (1995).
Marra et al., *EMBL Database*, Accession No. AA120122 (1996).
Martin et al., *Crit. Rev. Biochem. Mol. Biol.*, 26:377-395 (1991).
Mason et al., *Nature*, 318:659-663 (1985).
Massague et al., *Trends in Cell Biol.*, 4:172-178 (1994).
Massague et al., *Cell*, 69:1067-1070 (1992).
Massague et al., *Cell*, 49:437-438 (1987).
Mathews et al., *Cell*, 65:973-982 (1991).
Matsuzaki et al., *J. Biol. Chem.*, 268:12719-12723 (1993).
Matzuk et al., *Nature*, 360:313 (1992).
McConahey et al., *Int. Arch. Allergy*, 29:185-189 (1966).
McDonald et al., *Cell*, 73:421-424 (1993).
Miller et al., *J. Immunol.*, 143:2907 (1989).
Miller et al., *Genetic Engineering*, 8:277-298 (1986).
Miyazono et al., *Gen Bank Record No. Z23154* (1993).
Morii et al., *J. Biol. Chem.*, 258:12749-12752 (1983).
Mullins et al., *Nature*, 303:856-858 (1984).
Nabeshima et al., *Alz Dis. And Assoc. Disord. 14(Suppl. 1)*:S39-S46 (2000).
Nakamura et al., *J. Biol. Chem.*, 267:18924-18928 (1992).
Nakao et al., *Mol. Cell Biol.*, 10:3646-3658 (1990).
Nakatani T., *Jap. J. Clin. Med.*, 52:824-33 (1994).
Nathan et al., *J. Cell Biol.*, 113:981-986 (1991).
Neuhaus et al., *Mech. Dev.*, 80:181-184 (1999).
Nirschl, R., *American Orthopaedic Society for Sports Medicine*, Leadbetter, W. et al., eds, Ch. 13:577-585 (1989).

Ngo et al., *Merz et al., eds., Brickhauser, Boston*, Springer Verlag, pp. 433-434 & 492-495 (1994).
Noble et al., *J. Neuroscience*, 4:1892-1903 (1984).
Obaru et al., *J. Biochem.*, 99:885 (1986).
Ogawa et al., *J. Biol. Chem.*, 267:14233 (1992).
Ohura et al., *J. Biomed. Mat. Res.*, 30:193-200 (1996).
Ohura et al., *J. Biomed. Mat. Res.*, 44: 168-175 (1999).
Okayama et al., *Mol. Cell Biol.*, 2:161-170 (1982).
Ozkaynak et al., *EMBO Journal*, 9:2085-2093 (1990).
Padgett et al., *Nature*, 325:81-84 (1987).
Paralkar, et al., *J. Cell Biol.*, 119:1721-1728 (1992).
Park et al., *J. Biol. Chem.*, 271:8161-9 (1996).
Patel et al., Pharmacotherapy of Cognitive Impairment in Alzheimer's Disease: A Review:81-95 (1992).
Perides et al., *J. Biol. Chem.*, 269:765-770 (1994).
Perides et al., *PNAS*, 89:10326-10330 (1992).
Peyron, J.G. *J. Rheumatol. Suppl.*, 27:2-3 (1991).
Pierce et al., *J. Clin. Investig.*, 96:1336-50 (1995).
Pollock, *J. Biol. Chem.*, 271:8008-14 (1996).
Pragnell et al., *Blood*, 72:196-201 (1988).
2001-2002 Progress Report on Alzheimer's Disease, *National Institute on Aging; NIH*:1-51 (2002).
Rabin et al., *Mol. Cell. Biol.*, 13:2203-2213 (1993).
Ralph et al., *Cancer Res.*, 37:546 (1977).
Ralph et al., *J. Immunol.*, 114:898 (1975).
Rattner et al., *PNAS*, 94:2859-2863 (1997).
Reddi, A. *JBJS*, 83-A:S1-1:S1-S6 (2001).
Reddi et al., *Osteoporosis, Academic Press*, pp. 281-287 (1996).
Reddi et al., *PNAS*, 69:1601 (1972).
Reeck, *Cell*, 50:667 (1987).
Roberts et al., *PNAS*, 83:4167-4171 (1986).
Robertson et al., *Biochem. Biophys. Res. Commun.*, 149:744-749 (1987).
Rodeo et al., *Orthopaedic Res. Soc.*, 41$^{st}$ Annual Mtg, Orlando, Florida, p. 288 (1995).
Rodeo, et al., *J. Bone Joint Surg.*, 75-A:1795-1803 (1993).
Rosen et al., *Trends in Genetics*, 8:97-102 (1992).
Rosen et al., *Connect Tissue Res.*, 20:313-9 (1989).
Rubin et al., *Science*, 287:2204-2215 (2000).
Rudinger, *Peptide Hormones*, Parsons (ed.), U Park Press, Baltimore:1-7 (1976).
Sakai et al., *PNAS*, 87:8378-8382 (1990).
Salic et al., *Development*, 124:4739-4748 (1997).
Sambrook et al., *Mol. Cloning: A Laboratory Manual*, 2$^{nd}$ *Ed.*, vols. 1, 2 and 3, Cold Spring Harbor Laboratory Press: Cold Spring Harbor, New York, USA (1989).
Sampath et al., *J. Biol Chem.*, 267:20352-20362 (1992).
Sampath et al., *J. Biol Chem.*, 265:13198-13205 (1990).
Sampath et al., *PNAS*, 84:7109-7113 (1987).
Sampath et al., *PNAS*, 80:6591-6595 (1983).
Sampath et al., *Exp. Cell. Res.*, 143:460-64 (1982).
Sato et al., *Clin. Orthopaedics Related Res.*, 183:180-187 (1984).
Saukkonon et al., *J. Exp. Med.*, 171:439 (1990).
Schubert et al., *Nature*, 344:868-870 (1990).
Schulz et al., *Principles of Protein Structure*, Springer-Verlag New York, Inc., New York:14-16 (1979).
Shah, et al., *J. Cell Sci.*, 108:985-1002 (1995).
Shimasaki et al., *PNAS*, 85:4218-4222 (1988).
Shipley et al., *Cancer Res.*, 46:2068-2071 (1986).
Shoda et al., *Growth Factors*, 8:165-172 (1993).
Smith et al., *Brain Res.*, 543:111-122 (1991).
Smith et al., *Dev. Biol.*, 138:377-390 (1990).
Smith et al., *J. Neurochem.*, 60:1453-1466 (1993).
Sompayrac et al., *PNAS*, 78:7575-7578 (1981).
Song et al., *Mol. Biol. Cell*, 5:384a (1994) and 34$^{th}$ Ann. Mtg of the American Soc. for Cell Biol., San Francisco, CA (1994).
Sporn et al., *Nature*, 332:217-219 (1988).
Sporn et al., *Science*, 233:532-534 (1986).
Storm et al., *Nature*, 368:639-642 (1994).
Sugino et al., *J. Biol. Chem.*, 268:15579 (1993).
Suggs et al., *PNAS*, 78:6613-6617 (1981).
Sumitomo et al., *Biochem. Biophys. Acta.*, 208:1 (1995).
Sumitomo et al., *DNA Sequence-J. DNA Sequence and Mapping* 3:297-302 (1993).
Suzuki et al., *Proc Natl Acad Sci USA* 91:10255-59 (1994).
Tabas et al., *Genomics*, 9:283-289 (1991).
Takagi et al., *Clin. Orthopaed. Related Res.*, 171:224-231 (1982).
Taniguchi et al., *PNAS*, 77:5230-5233 (1980).
Tatusova et al., *FEMS Microbiol. Lett.*, 174:247-250 (1990).
Ten Dijke et al., *J. Biol. Chem.*, 269:16985-16988 (1994).
Ten Dijke et al., *EMBL Z22534* (Apr. 6, 1993).
Ten Dijke et al., *EMBL Sequence Database, European Molecular Biology Laboratory (Basel, CH)*, Accession No. Z22535 (1993).
Ten Dijke et al., *EMBL Sequence Database, European Molecular Biology Laboratory (Basel, CH)*, Accession No. Z22536 (1993).
Thies et al., *J. Bone Min. Res.*, 5:305 (1990).
Thies et al., *Endocrinol.*, 130:1318-1324 (1992).
Thomsen et al., *Trends in Genetics*, 13:209-211 (1997).
Thomsen et al., *Cell*, 74:433-441 (1993).
Tona et al., *J. Histochem. Cytochem.*, 41:591-599 (1993).
Toriumi et al., *Arch. Otolaryngol. Head Neck Surg.*, 117:1101-1112 (1991).
Tsuchida et al., *PNAS*, 90:11242-11246 (1993).
Tsukazaki et al., *Calcif. Tissue Int.*, 57:196-200 (1995).
Tuszynski, *Cell Transplantation*, 9:629-636 (2000).
Ueno et al., *PNAS*, 84:8282-8286 (1987).
Ulrich et al., *EMBO J.*, 3:361-364 (1984).
Urdal et al., *PNAS*, 81:6481-6485 (1984).
Urist et al., *Fed. Proceed.*, Bethesda, MD, US, 3:746 (1985).
Urist et al., *PNAS*, 81:371-375 (1984).
Urist et al., *Clin. Orthopaed. and Related Res.*, 187: 277-280 (1984).
Urist et al., *Proc. Soc. Exper. Biol. & Med.*, 2:194 (1983).
Urist et al., *Science*, 220:680-686 (1983).
Urist et al., *PNAS*, 70:3511 (1973).
Urist et al., *Clin. Orthoped. Rel. Res.*, 214:295-304 (1986).
Urlaub et al., *PNAS*, 77:4216-20 (1980).
Vukicevic et al. *PNAS*, 93:9021-6 (1996).
Wall et al., *J. Cell Biol.*, 120:493-502 (1993).
Wang et al., *Cell*, 67:797-805 (1991).
Wang et al.,*J. Cell Biochem.*, Suppl. 15, Part E, p. 161, Abstract Q020 (1991).
Wang et al., *PNAS*, 87:2220-2224 (1990).
Wang et al., *PNAS*, 85:9484-9488 (1988).
Wang, E.A., *Trends in Biotech.*, 11:379-383 (1993).
Wang et al., *Cell*, 88:757-766 (1997).
Wang et al., *Stroke*, 32:2170-2178 (2001).
Weeks et al., *Cell*, 51:861-867 (1987).
Wells, *Biochemistry*, 29:8509-8517 (1990).
Wharton et al., *PNAS*, 88:9214-9218 (1991).
Wolpe et al., *FASEB J.*, 3:2565-2573 (1989).
Wolpe et al., *J. Biochem. Suppl. O*, Abstract H141, 13 Part C:21 (1989).
Wolpe et al., *J. Exp. Med.*, 167:570 (1988).
Wong et al., *Science*, 228:810-815 (1985).
Woo et al., *PNAS*, 75:3688-3691 (1978).
Wood et al., *PNAS*, 82:1585-1588 (1985).
Wozney et al., *J. Cell Sci.*, Suppl. 13:149-156 (1990).
Wozney, *Mol. Reproduction & Develop.*, 32:160-167 (1992).
Wozney et al., *Science*, 242:1528-1534 (1988).
Wozney, J.M., *Prog. Growth Factor Res.*, 1:267-280 (1989).
Wozney et al., *Handbook of Exp. Pharm., eds.*, G.R. Mundy and T.J. Martin; Springer-Verlag, Berlin, Chapter 20, 107:725-748 (1993).
Wozney, *Cell. & Mol. Biol. Bone*, pp. 131-167 (1993) (Academic Press, Inc.).
Wozney et al., *J. Cell Biochem.*, Suppl. 16F:76 Abstract (1992).
Wozney *Spine*, 27:S2-S8 (2002).
Wright et al., *Leukemia Res.*, 4:537 (1980).
Wright et al., *Cell Tissue Kinet.*, 18:193 (1985).
Xu et al., *Proc Natl Acad Sci USA*, 91:7957-61 (1994).
Yamaguchi et al., *Nippon Rinsho*, 50:1932-1938 (1992).
Yamaji et al., *Biochem. Biophys. Res. Comm.*, 205:1944-1951 (1994).
Zipfel et al., *J. Immunol.*, 142:1582 (1989).
Zheng et al., *Path. Res. Pract.*, 188:1104-1121 (1992).
Zhou et al., *Nature*, 361:543-547 (1993).

Fleisch, Bisphosphonates In Disease, From the Laboratory to the Patient, 3rd Ed. Parthenon Publishing (1997).
International Preliminary Examination Report for PCT/US2004/029560.
International Search Report for PCT/US2004/029560.
Lee et al., Clin Orthop Rel Res 367S:S396-405 (1999).
U.S. Appl. No. 10/525,411, filed Feb. 22, 2005, Li et al., co-pending application.

U.S. Appl. No. 12/414,715, filed Mar. 31, 2009, Li et al., co-pending application.

International Search Report dated Aug. 5, 2005 for PCT/US04/029560.

* cited by examiner

INJECTABLE CALCIUM PHOSPHATE SOLID RODS AND PASTES FOR DELIVERY OF OSTEOGENIC PROTEINS

RELATED APPLICATIONS

This application claims priority to U.S. Provisional Application No. 60/502,493, filed Sep. 12, 2003, which is incorporated herein by reference.

FIELD OF THE INVENTION

The subject invention relates to the field of osteogenic proteins and pharmaceutical formulations thereof.

RELATED BACKGROUND ART

Idiopathic osteoporosis is a disease of unknown etiology characterized by progressive loss of bone mass and increased fragility, resulting in a marked increase in susceptibility to fractures. Osteoporosis is among the most prevalent of all musculoskeletal disorders, afflicting fifty six percent of women over 45 years of age. Praemer et al., "Musculoskeletal Conditions in the United States", Amer. Acad. of Orthopaedic Surgeons, Park Ridge, Ill. (1992). Because its incidence increases with age and the percentage of elderly in the population is increasing, osteoporosis will become more common with time. Osteoporosis is difficult to treat locally, and there is presently no known cure. Finally, and most significantly, osteoporosis is associated with a substantial morbidity and mortality. The most serious fracture resulting from osteoporosis is that the of the proximal femur in the region of the hip joint. With an annual incidence of over 300,000, hip fractures are currently the most common fracture in the elderly. One out of every six Caucasian women will have a hip fracture during her lifetime (Cummings et al., Arch. Intern. Med., vol. 149, pp. 2455-2458 (1989)), and for those who attain the age of 90, this figure becomes one in three.

In addition to treating osteoporotic bone, a need exists for methods of treating or preventing osteoporosis related fractures, for example, by local administration of osteogenic proteins. Osteogenic proteins are those proteins capable of inducing, or assisting in the induction of, cartilage and/or bone formation. Many such osteogenic proteins have in recent years been isolated and characterized, and some have been produced by recombinant methods.

In addition, various formulations designed to deliver osteogenic proteins to a site where induction of bone formation is desired have been developed.

But despite substantial endeavors in this field, there remains a need for an effective method of repair and/or treatment of osteoporotic and osteopenic bone and for minimizing or reducing the incidence or severity of osteoporosis related fractures.

SUMMARY OF THE INVENTION

The present invention is directed to compositions for injectable delivery of osteogenic proteins, i.e., osteogenic compositions. The compositions may take the form of a solid rod, preferably a cylindrical solid rod, or a hardenable paste. The compositions comprise an osteogenic protein and a calcium phosphate material.

In certain preferred embodiments of the present invention, the osteogenic protein is a member of the bone morphogenetic protein family, more preferably one of BMP-2, BMP-4, BMP-5, BMP-6, BMP-7, BMP-10, BMP-12, and BMP-13, most preferably BMP-2. The osteogenic protein is preferably present in an amount ranging from about 1% to about 90%, more preferably from about 15% to about 40%, by weight of the solid rods of the invention and in an amount ranging from about 0.01% to about 2%, more preferably from about 0.03% to about 1%, by weight of the paste of the invention.

In certain preferred embodiments of the present invention, the calcium phosphate material comprises a material selected from amorphous apatitic calcium phosphate, poorly crystalline apatitic calcium phosphate, hydroxyapatite, tricalcium phosphate, fluorapatite and combinations thereof. Most preferably, the calcium phosphate material is a poorly crystalline apatitic calcium phosphate. The calcium phosphate material is preferably present in an amount ranging from about 10% to about 99%, more preferably from about 40% to about 60%, by weight of the rod-shaped osteogenic composition and in an amount ranging from about 30% to about 70%, more preferably from about 45% to about 55%, by weight of the hardenable paste osteogenic composition.

Additional embodiments of the present invention are directed to osteogenic compositions which also comprise a bone resorption inhibitor. The bone resorption inhibitor is preferably a bisphosphonate selected from alendronate, cimadronate, clodronate, EB 1053, etidronates, ibandronate, neridronate, olpadronate, pamidronate, risedronate, tiludronate, YH 529, zoledronate, and pharmaceutically acceptable salts, esters, acids, and mixtures thereof.

Additional embodiments of the present invention are directed to osteogenic compositions which also comprise an additive selected from pharmaceutically acceptable salts, polysaccharides, peptides, proteins, amino acids, synthetic polymers, natural polymers, surfactants, and combinations thereof, more preferably selected from carboxymethylcellulose, hydroxypropylmethylcellulose, methylcellulose, polylactide, polyethylene glycol, polyvinylpyrrolidone, polyoxyethylene oxide, carboxyvinyl polymer, polyvinyl alcohol, dextran sulfate and combinations thereof. The additive is preferably present in an amount ranging from about 1% to about 90%, more preferably from about 20% to about 40%, by weight of the rod-shaped osteogenic composition and in an amount ranging from about 1% to about 90%, more preferably about 10% to about 20%, by weight of the hardenable paste osteogenic composition.

When the osteogenic composition of the present invention takes the form of a solid cylindrical rod, the diameter of the cylindrical rod is preferably between about 0.1 mm and 3.0 mm, more preferably about 1.0 mm, and the length of the cylindrical rod is preferably between about 0.5 cm and 5.0 cm.

An additional embodiment of the present invention is directed to a method for preparing a rod-shaped composition for injectable delivery of osteogenic proteins, said composition comprising an osteogenic protein and a calcium phosphate material, comprising the steps of (a) mixing a dry form of the osteogenic protein with a dry form of the calcium phosphate material to produce a dry mixture; (b) reconstituting the dry mixture by adding an aqueous buffer to form a paste; (c) molding the paste to form a rod shaped composition; and (d) drying the rod shaped composition of step (c) to form a rod-shaped composition for injectable delivery of osteogenic proteins. In preferred embodiments, the aqueous buffer is selected from phosphate-buffered saline, saline, glycine- and glutamic acid-based buffers and combinations thereof. The volume to weight (mL:g) ratio of aqueous buffer to dry mixture ranges from about 0.5:1 to about 2:1. Molding is preferably accomplished by molding, extruding, pressing, boring or combinations thereof. In certain preferred embodiments the rod-shaped composition is cut before or after step (d).

Yet another embodiment of the present invention is directed to a method for preparing a paste composition for injectable delivery of osteogenic proteins, said composition comprising an osteogenic protein and a calcium phosphate material, comprising the step of mixing a dry form of the calcium phosphate material with an aqueous buffer containing an osteogenic protein to form a paste. In preferred embodiments of the present invention, the aqueous buffer is selected from phosphate-buffered saline, saline, glycine- and glutamic acid-based buffers and combinations thereof. The ratio of aqueous buffer to calcium phosphate material ranges from about 0.5:1 to about 2:1.

Still further embodiments of the present invention are directed to methods of treating a mammal having a bone defect comprising administering to the site of the bone defect an effective amount of a composition for injectable delivery of osteogenic proteins claimed herein. Still further embodiments of the present invention are directed to methods of treating a mammal having a bone defect comprising the steps of (a) administering to the site of the bone defect an effective amount of a composition for injectable delivery of osteogenic proteins claimed herein and (b) administering to the site of the bone defect an effective amount of a bone resorption inhibitor. The administration of a bone resorption inhibitor can be performed prior to step (a), after step (a) or simultaneously with step (a).

DETAILED DESCRIPTION OF THE INVENTION

Generally, the methods and compositions of the present invention relate to the regeneration of bone tissue and concomitant increase of bone mass, bone density, and bone strength. More particularly, the subject invention involves injectable solid rods and pastes comprising an osteogenic protein, a calcium phosphate carrier and optional additives and active agents such as a bone resorption inhibitor, as well as methods of preparing such osteogenic compositions and methods of treating using such osteogenic compositions. The calcium phosphate solid rods and hardenable pastes of the present invention are suitable for intraosseous delivery of osteogenic proteins. Through the use of the present inventive methods and compositions, the severity of osteoporosis or the incidence of osteoporotic lesions can be advantageously lessened, ultimately lessening the incidence of bone fractures. Other clinical uses include fracture repair, cartilage repair, non-union defect repair and spinal fusion. The injectable solid rods and hardenable pastes of the present invention may also be used to promote bone growth as needed when using joint replacement implants as described in provisional U.S. Application No. 60/502,526, ("Promotion of Bone Ingrowth in Joint Replacement Implants Using Osteogenic Proteins; the subject matter of this provisional application is incorporated in its entirety by reference herein.

A first embodiment of the present invention is directed to a rod-shaped composition for injectable delivery of osteogenic proteins comprising an osteogenic protein and a calcium phosphate material. A composition according to this first embodiment of the present invention may optionally include other additives (binders, excipients) and/or active agents such as a bone resorption inhibitor.

This solid rod-shaped composition is suitable for local intraosseous delivery and may, therefore, be injected directly into an osteoporotic or osteopenic site to effectively induce the formation and/or maintenance of bone. Further, the injectable rod-shaped composition exhibits a sustained-release profile with regard to the osteogenic protein when delivered in this manner. Preferably the solid rods of the present invention are cylindrical and have a diameter ranging from about 0.1 mm to about 3.0 mm, more preferably about 1.0 mm so as to allow delivery by a 16-gauge needle. In addition, the solid rods preferably have a length ranging from about 1.0 mm to about 5.0 cm.

Unlike existing injectable formulations, the osteogenic composition of this first embodiment of the present invention is administered in a solid form, thereby avoiding the deficiencies inherent in liquid or viscous formulations. For example, using liquid or gel formulations, the osteogenic agent may be prematurely diluted by the body fluids before the bone promoting effect can be achieved. The present invention obviates the dilution effect by employing a solid carrier which degrades slowly in vivo, thereby providing delayed, sustained release of the active agent(s). Furthermore, unlike liquid or viscous formulations which may migrate from the site of administration, the solid compositions of the present invention become lodged and persist at the site of desired bone growth to effect the bone growth promoting activity. Also they allow a more precise injectable placement of a solid rod in areas of low bone mass. Typically, the composition should persist at the site for a period from about 5 days to about 2 months. If the composition is dispersed prematurely, the desired bone growth promotion effect either will not occur or the formed bone will not have the desired strength. Finally, although the osteogenic composition of this embodiment of the present invention is administered as a solid, it is preferably formed as a cylindrical rod, thereby being suitable for either injection or implantation into the body. Of course, if desired, other rod shapes could be used, e.g., hexagonal, square or semi-circular rod shapes. In addition, the well known surgical complication of inducing an embolism during an intraosseous injection procedure is considerably mitigated through the use of solid rods (vs. liquid or gel forms). The potential displacement of intraosseous bone fragments, fat or an embolism caused by a pressurized injection of a large volume of liquid/gel carrier is reduced since the volume injected of highly concentrated solid rod is much less than that required if a similar dose was dispensed in a liquid or gel form. The composition may be applied to the site of desired bone growth in any convenient manner, including by introduction through a conventional hypodermic needle or syringe.

A second embodiment of the present invention is directed to a method for preparing the solid rod-shaped composition for injectable delivery of osteogenic proteins. In the first step, a dry form of the osteogenic protein is mixed with a dry form of the calcium phosphate material to produce a dry mixture. In other words, powdered or dry forms of both the osteogenic protein and the calcium phosphate material are initially employed in order to form a dry mixture. When additives and/or additional active agents are included in the composition, these materials may also be employed in a dry or powdered form and included in the dry mixture.

In the second step, the dry mixture is reconstituted by adding an aqueous buffer to form a paste. Suitable aqueous buffers include, without limitation, phosphate-buffered saline, saline, glycine-based buffers and combinations thereof. When using BMP-2 as the osteogenic protein, a glycine-based buffer having a pH of about 4.5 is preferred for use; more preferably, a glycine-based buffer having a composition of 5 mmol L-glutamic acid, 2.5% glycine, 0.5% sucrose, 5 mmol NaCl and 0.01% polysorbate 80 is used.

A volume to weight (mL:g) ratio of aqueous buffer to dry mixture ranges from about 0.5:1 to about 2:1. However, the lower limit of this weight ratio is limited only by the concern that enough liquid be added to the dry mixture so as to be sufficient to allow the formation of a paste which can be formed through injection through a syringe or some other method. In addition, the upper limit of this weight ratio is limited only by the concern that not so much liquid be added to the dry mixture that, upon subsequent drying, the geometry achieved, i.e., rod shape, is disturbed; in other words, if too much liquid is used, then the rod shape formed in the third step of this method will be compromised upon drying the osteogenic compound.

This step is performed under conditions where substantially uniform mixing occurs. Mixing combines the ingredients and can be used to regulate the extent of inter-ingredient reactions. While all of the desired ingredients are preferably contained in the dry mixture, it is also possible to add an additive or an additional active agent immediately prior to the initiation of mixing or prior to the completion of mixing. Such an additive or additional active agent is preferably in a dry form; however, a hydrated form of the additive or additional active agent may also be added to the paste.

In the third step of the present inventive method, the paste is molded to form a rod shaped composition. Molding or shaping may be accomplished using any one of a number of known techniques such as molding, extruding, pressing, boring and/or cutting. In a preferred embodiment of this invention, the paste is packed into and extruded through the hub end of a hypodermic syringe. In this case, the plunger of the syringe is inserted and a sufficient amount of pressure is applied to extrude a continuous length of paste onto a dry surface. Sections are then cut using a cutting tool such as a razor, scalpel, knife or the like, to form injectable, rod-shaped compositions. Cutting may also take place after the drying step described below. Alternatively, the paste may be packed into a cylindrical mold, catheter, air or gas-permeable tubing (e.g., silastic or Teflon®/FEP), or any other extrusion-type apparatus.

In the final step, the rod shaped composition obtained in the previous step is dried or hardened to form the rod-shaped composition for injectable delivery of osteogenic proteins of the present invention (first embodiment). Drying may be accomplished via air drying or incubation at elevated temperatures, i.e., at least 37° C. The drying temperature is limited only by a concern for osteogenic protein degradation, which typically occurs somewhere in the range of 55° C. and 60° C. When drying is accomplished in a 37° C. oven, drying takes approximately at least one hour, and preferably drying is carried out overnight. The rod-shaped composition preferably has a residual moisture of less than 10%.

A third embodiment of the present invention is directed to a hardenable paste composition for injectable delivery of osteogenic proteins comprising an osteogenic protein and a calcium phosphate material. A composition according to this third embodiment of the present invention may optionally include other additives (binders, excipients) and/or active agents such as a bone resorption inhibitor.

This paste is suitable for local intraosseous delivery and may, therefore, be injected directly into an osteoporotic or osteopenic site whereupon the paste hardens to a solid form and effectively induces the formation and/or maintenance of bone. Because the paste hardens upon injection into an at least 37° C. environment, i.e., into a mammal, many of the disadvantages associated with the use of liquid or gel compositions are avoided. Similar to the solid rod-shaped injectable composition described above, the hardened paste composition exhibits a sustained-release profile with regard to the osteogenic protein. The injectable life of the hardenable paste may be prolonged by refrigerating the paste.

A fourth embodiment of the present invention is directed to a method for preparing the paste composition for injectable delivery of osteogenic proteins. In this method, a dry form of the calcium phosphate material is mixed with an aqueous buffer containing an osteogenic protein to form a paste. When additives and/or additional active agents are included in the composition, these materials may be employed in either dry form to be pre-mixed with the dry form of calcium phosphate material or in a hydrated form to be mixed directly with the aqueous buffer and the calcium phosphate material. Mixing is performed under conditions where substantially uniform mixing occurs. Mixing combines the ingredients and can be used to regulate the extent of inter-ingredient reactions.

Suitable aqueous buffers include, without limitation, phosphate-buffered saline, saline, glycine-based buffers and combinations thereof. When using BMP-2 as the osteogenic protein, a glycine-based buffer having a pH of about 4.5 is preferred for use; more preferably, a glycine-based buffer having a composition of 5 mmol L-glutamic acid, 2.5% glycine, 0.5% sucrose, 5 mmol NaCl and 0.01% polysorbate 80 is used. A weight ratio of aqueous buffer to dry calcium phosphate ranges from about 0.5:1 to about 2:1.

Alternatively, a dry form of the osteogenic protein is mixed with a dry form of the calcium phosphate material to produce a dry mixture, and the dry mixture is then reconstituted by adding an aqueous buffer to form a paste. These steps would be identical to the first and second steps of the method of preparing the solid rod-shaped composition above (second embodiment) except that a weight ratio of aqueous buffer to dry calcium phosphate ranges from about 0.5:1 to about 2:1.

Details regarding the active agent, carrier, additives and bone resorption inhibitors suitable for use in the present invention are given below.

Active Agent

The active agent present in the osteogenic compositions of the present invention is preferably selected from the family of proteins known as the transforming growth factors beta (TGF-β) superfamily of proteins. This family includes the activins, inhibins and bone morphogenetic proteins (BMPs). These BMPs include BMP-proteins BMP-2, BMP-3, BMP-4, BMP-5, BMP-6, and BMP-7, disclosed, for example, in U.S. Pat. Nos. 5,108,922, 5,013,649, 5,116,738, 5,106,748, 5,187,076, and 5,141,905, BMP-8, disclosed in PCT WO 91/18098, BMP-9, disclosed in PCT WO 93/00432, BMP-10, disclosed in PCT WO 94/26893, BMP-11, disclosed in PCT WO 94/26892, BMP-12 and BMP-13, disclosed in PCT WO 95/16035, BMP-15, disclosed in U.S. Pat. No. 5,635,372, and BMP-16, disclosed in U.S. Pat. No. 6,331,612. Other TGF-β proteins which may be useful as the active agent in the present invention include Vgr 2, Jones et al., Mol. Endocrinol., vol. 6, pp. 1961 1968 (1992), and any of the growth and differentiation factors (GDFs) including those described in PCT WO 94/15965, WO 94/15949, WO 95/01801, WO 95/01802, WO 94/21681, WO 94/15966, WO 95/10539, WO 96/01845, WO 96/02559 and others. Also useful in the present invention may be BIP, disclosed in WO 94/01557, HP00269, disclosed in JP 7 250688, and MP52, disclosed in PCT WO 93/16099. The disclosures of all of the above patents, journal publications and published international applications are incorporated by reference herein.

Preferably, the active agent includes at least one protein selected from the subclass of proteins known generally as BMPs, which have been disclosed to have osteogenic activity, and other growth and differentiation type activities. A subset of BMPs which are presently preferred for use in the present invention include BMP-2, BMP-4, BMP-5, BMP-6, BMP-7, BMP-10, BMP-12, and BMP-13, most preferably BMP-2, the sequence of which is disclosed in U.S. Pat. No. 5,013,649, the disclosure of which is incorporated by reference herein.

The active agent may be recombinantly produced or purified from a protein composition. The active agent, if a TGF-β such as a BMP, or other dimeric protein, may be homodimeric or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP-and a related member of the TGF-β superfamily). Examples of such heterodimeric proteins are described, for example, in PCT WO 93/09229, the disclosure of which is incorporated by reference herein. The active agent may comprise DNA encoding for BMPs and cells transduced or transfected with genes encoding BMP-proteins.

The active agent may further comprise additional agents such as the Hedgehog, Frazzled, Chordin, Noggin, Cerberus and Follistatin proteins. These families of proteins are generally described in Sasai et al., Cell, vol. 79, pp. 779-790 (1994) (Chordin); PCT WO 94/05800 (Noggin); and Fukui et al., Dev. Biol., vol. 159, pp. 131-139 (1993) (Follistatin). Hedgehog proteins are described in PCT WO 96/16668, WO 96/17924, and WO 95/18856. The Frazzled family of proteins is a relatively recently discovered family of proteins with high homology to the extracellular binding domain of the receptor protein family known as Frizzled. The Frizzled family of genes and proteins is described in Wang et al., J. Biol. Chem., vol. 271, pp. 4468-4476 (1996). The active agent may also include other soluble receptors, such as the truncated soluble receptors disclosed in PCT WO 95/07982. From the teaching of WO 95/07982, one skilled in the art will recognize that truncated soluble receptors can be prepared for numerous other receptor proteins. Such would also be encompassed within the present invention. The above publications are hereby incorporated by reference herein.

The amount of active agent useful herein is that amount effective to stimulate increased osteogenic activity of present or infiltrating progenitor (osteoblast precursor cells) or other cells (hereinafter "effective amount") and will depend upon the size and nature of the defect being treated, as well as the composition of the calcium phosphate carrier being employed. Generally, the amount of osteogenic protein present in a solid rod-shaped osteogenic composition of the present invention ranges from about 1% to about 90%, more preferably from about 15% to about 40%, by weight of the osteogenic composition. Generally, the amount of osteogenic protein present in a hardenable paste osteogenic composition of the present invention ranges from about 0.01% to about 2%, more preferably from about 0.03% to about 1%, by weight of the osteogenic composition.

Carrier

According to all embodiments of the present invention, a calcium phosphate material is employed as a carrier. As used herein, a "calcium phosphate material" means any synthetic bone substitute material comprising calcium phosphate as the primary component, i.e., having at least 90% by weight attributable to calcium and/or phosphate. The calcium phosphate material of the present invention may be any biocompatible, calcium phosphate material known in the art. Suitable calcium phosphate materials may be produced by any one of a variety of methods and using any suitable starting components or may be commercially available.

In certain preferred embodiments of the present invention, the calcium phosphate material is present in an amount ranging from about 10% to about 99%, more preferably from about 40% to about 60%, by weight of the solid rod-shaped osteogenic composition of the present invention. In certain other preferred embodiments of the present invention, the calcium phosphate material is present in an amount ranging from about 30% to about 70%, more preferably from about 45% to about 55%, by weight of the hardenable paste osteogenic composition of the present invention. Preferably, the calcium phosphate material or carrier is used in dry, i.e., powdered, form.

Forms of calcium phosphate suitable for use in this invention include, without limitation, amorphous apatitic calcium phosphate (ACP), poorly crystalline apatitic calcium phosphate (PCA), hydroxyapatite (HA), tricalcium phosphate and fluorapatite. In a preferred embodiment, the calcium phosphate material is a poorly crystalline apatitic calcium phosphate solid having a calcium-to-phosphate (Ca/P) ratio comparable to naturally occurring bone minerals, more preferably a calcium-to-phosphate ratio of less than about 1:1.5, most preferably about 1:1.4.

Suitable PCA materials may be identified by combining PCA precursors, hydrating with a limited amount of water (so that a paste or putty is formed), molding into a cylindrical rod shape, and allowing the molded material to harden into a PCA material. Desirable precursors are capable of hardening in a moist environment, at or around body temperature in less than 5 hours and preferably within 10-30 minutes.

According to the present invention, the calcium phosphate carrier may comprise any bone substitute material which contains one of the above forms of calcium phosphate as its primary component, i.e. having at least 90% by weight attributable to calcium and/or phosphate. The bone substitute material may comprise solely one of the above forms of calcium phosphate, with or without additional components; the bone substitute may comprise a combination of the above forms of calcium phosphate, with or without additional components. In addition, one or more of the above-noted forms of calcium phosphate may be used to prepare a calcium phosphate material suitable for use in the present invention. Methods of making such materials are well known in the art. However, any method which results in obtaining a dry calcium phosphate material, i.e., powdered, is appropriate.

As used herein, "amorphous" means a material with significant amorphous character. Significant amorphous character contemplates greater than 75% amorphous content, preferably greater than 90% amorphous content, and is characterized by a broad, featureless X-ray diffraction pattern.

"Poorly crystalline apatitic calcium phosphate," "PCA calcium phosphate" and "PCA material," as those terms are used herein, describe a synthetic poorly crystalline apatitic calcium phosphate. The poorly crystalline apatitic (PCA) material is not necessarily restricted to a single calcium phosphate phase provided it has the characteristic X-ray diffraction (XRD) and fourier transform infrared (FTIR) pattern. A PCA calcium phosphate has substantially the same XRD spectrum as bone. The XRD spectrum is generally characterized by only two broad peaks in the region of 20-35E with one centered at 26E and the other centered at 32E. The FTIR spectrum is characterized by peaks at 563 cm$^{-1}$, 1034 cm$^{-1}$, 1638 cm$^{-1}$ and 3432 cm$^{-1}$ (±2 cm$^{-1}$); sharp shoulders are observed at 603 cm$^{-1}$ and 875 cm$^{-1}$, with a doublet having maxima at 1422 cm$^{-1}$ and 1457 cm$^{-1}$. PCA materials preferred for use in the present invention are described in U.S. Pat. Nos. 5,650,176, 5,683,461 and 6,214,368, each of which is incorporated by reference herein. Suitable materials are also described in a set of related applications, entitled "Delivery Vehicle," "Conversion of Amorphous Calcium Phosphate to Form a Novel Bioceramic," "Orthopedic and Dental Ceramic Implants," and "Bioactive Ceramic Composites," each of which was filed on Oct. 16, 1997 and assigned to ETEX Corporation (Cambridge, Mass.) and is incorporated by reference herein. In light of the breadth of disclosure in each of these above-noted patent documents, details of the production of suitable PCA materials will not be detailed here. A summary of PCA characteristics will suffice. PCA material is characterized by its bioresorbability and its minimal crystallinity. Its crystalline character is substantially the same as natural bone. PCA material also is biocompatible and not detrimental to the host.

Crystalline hydroxyapatite (HA) is described, for example, in U.S. Pat. Re. Nos. 33,221 and 33,161, both of which are incorporated by reference herein. These patents teach the preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905, both of which are incorporated by reference herein. Additional crystalline HA materials (commonly referred to as dahllite) are described in U.S. Pat. No. 5,962,028, the disclosure of which is incorporated by reference herein.

Additives

Additives may be useful in the osteogenic compositions of the present invention. Many such binders, which enhance cohesiveness, and excipients, which stabilize and/or modulate release of active ingredients, are well known in the formulation art. Suitable additives include, without limitation, pharmaceutically acceptable salts, polysaccharides, peptides, proteins, amino acids, synthetic polymers, natural polymers, and/or surfactants. Useful polymers include, for example, those described in U.S. Pat. No. 5,171,579, the entire disclosure of which is incorporated by reference herein. Preferred additives include cellulosic materials such as carboxymethylcellulose (CMC), hydroxypropylmethylcellulose (HPMC), and methylcellulose (MC), synthetic polymers such as polylactides and polyethylene glycols, e.g., polylactide/polyethylene glycol, polyvinylpyrrolidone (PVP), polyethylene glycol (PEG), polyoxyethylene oxide, carboxyvinyl polymer and polyvinyl alcohol (PVA), and dextran sulfate and combinations thereof. Other useful additives include, without limitation, sodium alginate, chitosan, collagen, gelatin, hyaluronan, and various peptides, proteins, and amino acids. Additives which have an effervescent effect are not presently intended for use in the present invention.

In a preferred embodiment of the present invention, an additive is employed in a dry or powder form, which is mixed with the active agent(s), carrier and aqueous liquid in order to prepare the injectable composition of the present invention. In certain preferred embodiments of the present invention, additive(s) is present in an amount ranging from about 1% to about 90%, more preferably from about 20% to about 40%, by weight of the solid rod osteogenic composition. In certain preferred embodiments of the present invention, additive(s) is present in an amount ranging from about 1% to about 90%, more preferably from about 10% to about 20%, by weight of the hardenable paste osteogenic composition.

Additional Active Agents

The injectable osteogenic compositions of the present invention may also include an additional active agent or additional active agents. Such additional active agents may be mixed, preferably in dry form though hydrated forms are also suitable for use, with the active agent, carrier and aqueous liquid in order to prepare the injectable osteogenic compositions of the present invention. Alternatively, such additional active agents may be co-administered with the osteogenic compositions of the present invention, either in some sequential manner or simultaneously (hereinafter "co-administration scheme"). Additional active agents may be employed herein in order to achieve additional desired effects or, in some cases, may be employed to counter potential undesirable effects, such as infection, inflammation and transient resorption.

For example, although much is known about the osteogenic potential of TGF-β proteins, recent reports show that local administration of certain osteoinductive agents, such as BMP-2, stimulates transient osteoclastic activity (local areas of bone resorption) at the site of administration. This reaction, which occasionally precedes new bone formation induced by the BMP, has been termed "transient resorption phenomenon." Agents known to inhibit bone resorption may, therefore, play an important role in delaying or reducing the initial bone resorption associated with local BMP-administration, without inhibiting subsequent bone formation.

Thus, in preferred embodiments of the present invention, a bone resorption inhibitor is employed as an additional active agent present in the injectable osteogenic composition or is co administered with the injectable osteogenic composition in order to prevent or minimize the initial bone resorption associated with intraosseous delivery of an active agent such as BMP. As used herein, the term "inhibition of bone resorption" refers to prevention of bone loss, especially the inhibition of removal of existing bone through direct or indirect alteration of osteoclast formation or activity. Thus, the term "bone resorption inhibitor" as used herein refers to agents that prevent or inhibit bone loss by the direct or indirect alteration of osteoclast formation or activity.

In certain preferred embodiments, the bone resorption inhibitor is a biphosphonate. As used herein, the term "bisphosphonate" refers to the related bisphosphonic acids and salts, and various crystalline and amorphous forms of bisphosphonate. Clinically, bisphosphonate therapy has been shown to dramatically reduce indices of bone turnover, increase bone mineral density, and, in osteopenic women, reduce hip and spine fracture risk (see, for example, H. Fleisch, Bisphosphonates in Bone Disease, from the Laboratory to the Patient, 3rd ed., Parthenon Publishing (1997), which is incorporated by reference herein).

Biphosphonates suitable for use in the present invention include, without limitation, alendronate, cimadronate, clodronate, EB 1053, etidronates, ibandronate, neridronate, olpadronate, pamidronate, risedronate, tiludronate, YH 529, zoledronate, and pharmaceutically acceptable salts, esters, acids, and mixtures thereof. The amount of biphosphonate, and indeed the amount of any bone resorption inhibitor, useful is that amount effective to prevent or inhibit the transient bone loss occasionally associated with the local administration of an osteogenic protein such as BMP-(hereinafter "effective amount"), by the direct or indirect alteration of osteoclast formation or activity. The precise dosage necessary will depend upon the size and nature of the bone defect being treated, as well as the amount of osteogenic agent being delivered. Generally, the amount of biphosphonate to be delivered is preferably in a range of from about 0.1 to about 3000 mg, more preferably about 10 to about 1000 mg, and most preferably about 10 to about 500 mg per cubic centimeter of material.

When the co-administration scheme of the present invention is employed, the bone resorption inhibitor is typically delivered in a suitable carrier. The carrier may be any pharmaceutically acceptable carrier, a wide variety of which are well known and readily available in the art (see, for example, Martin, E. W., Remington's Pharmaceutical Sciences (Mack Pub. Co., current edition), which is hereby incorporated by reference herein). Presently preferred carriers are formed into solid rods or pastes, as described elsewhere herein.

In the co-administration scheme, the bone resorption inhibitor may be administered sequentially, either before or after, or concurrently with the injectable solid rod or paste compositions of the present invention. In addition, the bone resorption inhibitor may be applied locally (intraosseous), but may be applied to other parenteral sites such as intramuscular or subcutaneous or ingested orally or injected intravenously for systemic delivery. Preferably the bone resorption inhibitor, e.g., a bisphosphonate, is delivered systemically, i.e., orally or intravenously, either before or concurrently with the injectable solid rod or paste composition of the present invention. Further, the bone resorption inhibitor may be implanted at the site to be treated by surgical implantation. It should be noted, however, that despite their therapeutic benefit, bisphosphonates are poorly absorbed in the gastrointestinal tract when taken orally. To overcome this poor bioavailability issue, intravenous administration has been used; however, this modality is seen as costly and inconvenient due to the duration and frequency of dosing. The present invention, therefore, can overcome this deficiency by incorporating the bisphosphonate within the injectable osteogenic compositions of the present invention and delivering it locally directly to the site of desired action.

The above description related to the administration of a bone resorption inhibitor relates generally to the administration of any additional active agent. Other suitable additional active agents include, without limitation, other osteogenic proteins, antibiotics, anti-inflammatory agents, growth factors, peptides, proteins, cytokines, oligonucleotides, antisense oligonucleotides, DNA and polymers. These compounds may be added, preferably in dry form, by mixing them to form the paste in the preparation methods of the present invention.

Administration

According to the present invention, methods and compositions are provided for treatment of patients who exhibit bone defects. As used herein, "bone defects" include osteoporotic bone, osteopenic bone, bone fracture, cartilage defect, and any other bone- or cartilage-related condition which would be improved or corrected with stimulated bone or cartilage growth. Therefore, a fifth embodiment of the present invention is directed to a method of treating a mammal having a bone defect by administering to the site of the bone defect an effective amount of an injectable rod or paste composition of the present invention.

A related sixth embodiment of the present invention is directed to a method of treating a mammal having a bone defect by administering to the site of the bone defect an effective amount of an injectable rod or paste composition of the present invention and by administering an effective amount of a bone resorption inhibitor. The bone resorption inhibitor may also be administered to the site of the bone defect, but can be administered by some other route, i.e., parenteral, surgical implantation, oral, intravenous. In addition, the administration of the bone resorption inhibitor may occur prior to, concurrent with or after the administration of the injectable rod or paste composition of the present invention.

Most commonly, the methods and compositions of the present invention are provided for the treatment of patients who exhibit signs of osteoporosis or osteopenic conditions, including osteoporotic bone lesions. The identification of such patients may be accomplished by procedures which are well known in the art. Such procedures provide the clinician with information on the location and severity of osteoporotic or osteopenic bone lesions. In addition to locating the lesion(s) to be treated, the clinician can use this information to select the appropriate mode of administration and dose of osteoinductive agent for the patient. Useful diagnostic procedures include measurement of bone mass/density using dual energy X ray absorptiometry (DEXA), Kilgus, et al., J. Bone & Joint Surgery, vol. 75 B, pp. 279-287 (1992); Markel, et al., Acta Orthop. Scand., vol. 61, pp. 487 498 (1990); and quantitative computed tomography (QCT), Laval Jeantet, et al., J. Comput. Assist. Tomogr., vol. 17, pp. 915-921 (1993); Markel, Calcif. Tissue Int., vol. 49, pp. 427-432 (1991); single photon absorptiometry, Markel, et al. Calcif. Tissue Int., vol. 48, pp. 392-399 (1991); ultrasound transmission velocity (UTV); Heaney, et al., JAMA, vol. 261, pp. 2986-2990 (1989); Langton, et al., Clin. Phys. Physiol. Meas., vol. 11, pp. 243-249 (1990); and radiographic assessment, Gluer, et al., J. Bone Min. Res., vol. 9, pp. 671-677 (1994). Other methods of identification of patients at risk of bone fracture include assessment of age related factors, such as cognisance, as well as prior occurrence of osteoporosis related fractures. Porter, et al., BMJ, vol. 301, pp. 638-641 (1990); Hui, et al., J. Clin. Invest., vol. 81, pp. 1804-1809 (1988). The above publications are hereby incorporated by reference herein.

Particular dosage regimens will be determined by the clinical indication being addressed, as well as by various patient variables (e.g. weight, age, sex) and clinical presentation (e.g. extent of injury, site of injury, etc.).

The injectable osteogenic compositions of the present invention may be administered in any clinically acceptable manner of injection. A number of commercially available syringes may be suitable for use in the present invention, and for administration of the compositions of the present invention. Such syringes include, without limitation, the Calasept® syringe (JS Dental Manufacturing, Ridgefield Conn.); the Henke-Ject® aspirating syringe and Hypo® dental syringes/needles (Smith & Nephew MPL, Franklin Park, Ill.); intraosseous needles from MPL, Inc., Chicago Ill.; and Luer-Lok® Syringes (Becton Dickinson, Franklin Lakes, N.J.). Any syringe capable of holding and delivering a paste or an injectable rod and/or enabling extrusion with an obdurator is appropriate for use.

In one embodiment of the invention, the solid rod shaped compositions are delivered intraosseously using an appropriate size and type hypodermic needle percutaneously or surgically preplaced into the selected anatomic location. Percutaneous placement of the hypodermic needle may be accomplished using manual palpation of known anatomic landmarks, with or without the use of fluoroscopy for visualize placement. Fluoroscopy may also be used in conjunction with surgical implantation prior to and/or concurrent with placement of the hypodermic needle.

In a preferred embodiment, a guide wire (commonly referred to as a "k wire") is first inserted percutaneously into the desired anatomic location to serve as a guide for the hypodermic needle. The hypodermic needle is inserted over the guide wire, which is subsequently removed leaving only the hypodermic needle in place. The solid rod shaped composition is then inserted into the hub end of the hypodermic needle. Following loading of the composition, a second guide wire is inserted into the needle, which is used to advance the solid composition to the tip of the needle. The needle is then removed leaving the guide wire to anchor the composition within the bone at the desired location. Finally, the guide wire is removed leaving the solid composition in place. In another embodiment, the solid rod shaped composition of the invention is preplaced within the needle barrel. After placement into the desired anatomic site, the plunger of the syringe is advanced into the needle barrel as the device is withdrawn, leaving the solid rod shaped composition at the desired location.

The compositions of the subject invention allow therapeutically effective amounts of osteogenic protein to be delivered to an injury site where cartilage and/or bone formation is desired. The formulations may be used as a substitute for autologous bone graft in fresh and non-union fractures, spinal fusions, and bone defect repair in the orthopaedic field, in cranio/maxillofacial reconstructions, in osteomyelitis for bone regeneration, and in the dental field for augmentation of the alveolar ridge and periodontal defects and tooth extraction sockets.

The following examples are illustrative of the present invention and are not limiting in any manner. Modifications, variations and minor enhancements are contemplated and are within the scope of the present invention.

EXAMPLES

All materials utilized in these examples are pharmaceutical grade. The calcium phosphate material was the commercially available bone substitute material (hereinafter "α-BSM") sold under the tradename CEREDEX™ by Etex Corporation, 38 Sydney Street, Cambridge, Mass. 02139 and described in detail in U.S. Pat. Nos. 5,683,461, 6,117,456 and 6,214,368 and PCT WO 98/16209. The osteogenic protein utilized as an active agent was recombinant human bone morphogenetic protein-2 (rhBMP-2). The production and characterization of rhBMP-2 is well known. Wang, et al., Proc. Nat'l Acad. Sci. U.S.A., vol. 87, pp. 2220-2224 (1990).

Example 1

Formulation

[66] Various injectable solid rods (A-E) of α-BSM, rhBMP-2, and one of carboxymethylcellulose (CMC), polyvinylpyrrolidone (PVP) and dextran sulfate were prepared. Dry powders of each component were combined in a sterile mixing bulb and reconstituted into a stiff putty by the addition of a a glycine-based aqueous buffer having a pH of about 4.5 and comprising 5 mmol L-glutamic acid, 2.5% glycine, 0.5% sucrose, 5 mmol NaCl and 0.01% polysorbate 80 at a specified liquid (ml) to powder (g) ratio (L/P) and kneaded for 1 minute to form a paste. The amounts of each ingredient, as well as the particular L/P ratios employed, were as set forth in Table 1 below.

TABLE 1

| rod | α-BSM (wt %) | | rhBMP-2 (wt %) | L/P ratio |
|---|---|---|---|---|
| | | CMC (wt %) | | |
| A | 68 | 17 | 15 | 1.0 |
| B | 56 | 29 | 15 | 1.2 |
| C | 45 | 40 | 15 | 1.5 |
| | | PVP (wt %) | | |
| D | 45 | 40 | 15 | 0.6 |
| | | dextran sulfate (wt %) | | |
| E | 45 | 40 | 15 | 0.6 |

Each paste was loaded into a syringe and extruded to form cylindrical rods having a diameter of about 1 mm and a length of about 5 cm. These 5 cm rods were then cut to desired lengths for testing below.

Following molding, the rods were hardened into a solid mass under simulated in vivo conditions, i.e., 37° incubator, overnight. The hardening process could be delayed for several hours by storing the rods at a cooler temperature, i.e., about 4° C.

The theoretical rhBMP-2 dose of each of rods A-E was 150 micrograms rhBMP-2 per milligram rod. All rods appeared to be smooth, dense, cohesive and non-brittle and were injectable through a 16-gauge needle.

Example 2

In vitro Characterization

A correlation was observed between additive content and particle formation. Upon submersion in the glycine-based aqueous buffer described in Example 1 for 14 days, rods containing higher % additive (40% CMC, 40% PVP, or 40% dextran sulfate, i.e., rods C-E, respectively) dispersed into smaller particles faster, i.e., within 1 day, than those with medium (29% CMC, i.e., rod B) and low (17% CMC, i.e., rod A) additive contents. Rods containing low additive contents (17% CMC, i.e., rod A) maintained their rod-like structure much longer, i.e., on the order of days to weeks, than their higher CMC counterparts.

Figure 1:
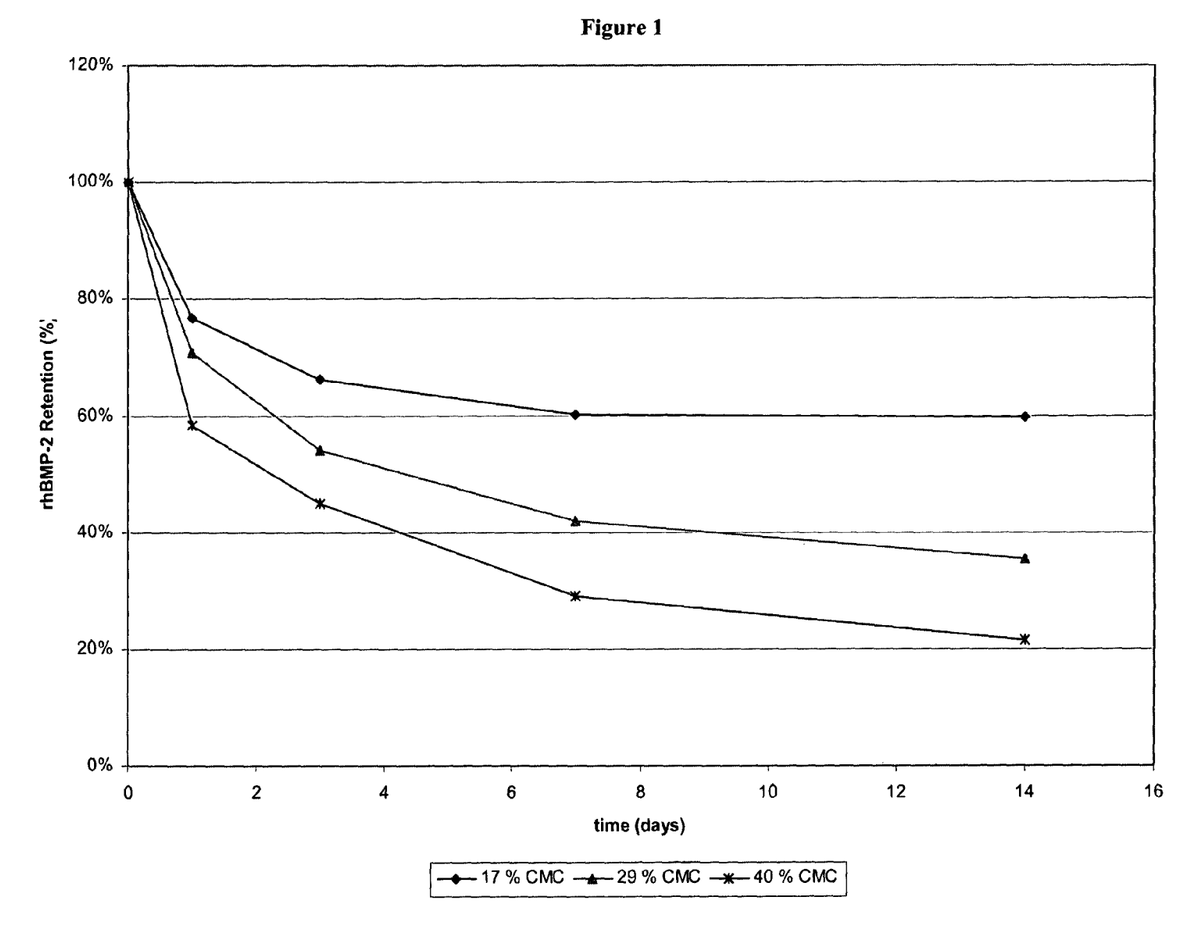
FIG. 1 is a graph showing the in vitro release kinetics of rhBMP-2 from α-BSM rods using 125I-rhBMP-2 as a tracer.

In addition, in vitro release kinetics of rhBMP-2 from α-BSM rods containing either 17% (rod A), 29% (rod B), or 40% (rod C) CMC was performed using 125I-rhBMP-2 as a tracer. Similar to gross observations, rods containing higher % CMC released rhBMP-2 faster than those with lower % CMC as shown in FIG. 1.

Example 3

Rat Biocompatibility and Efficacy Study

Injectable rod-shaped calcium phosphate-based compositions (prepared as described in Example 1) were evaluated for biocompatibility and efficacy, both intraosseous and ectopic, in a rat model.

Intraosseous core defects were surgically established in the distal femurs of six male CD rats. The rats were divided into two groups (A and B) of three. One limb from each rat received a 2 mm segment test rod (calcium phosphate/rhBMP-2/excipient), while the contralateral limb received a 2 mm segment control rod (calcium phosphate/excipient). The rats of Group A received rod A (68/17/15 (w/w) % ACP/

CMC/rhBMP-2) of Example 1 as the test rod, while the rats of Group B received rod B (56/29/15 (w/w) % ACP/CMC/rhBMP-2) of Example 1 as the test rod. In addition, one 10 mm rod was implanted subcutaneously lateral to the midline of the ventral thorax region, with one side receiving a test rod and the other side receiving a control rod. Here again, the rats of Group A received rod A (68/17/15 (w/w) % ACP/CMC/rhBMP-2) of Example 1 as the test rod, while the rats of Group B received rod B (56/29/15 (w/w) % ACP/CMC/rhBMP-2) of Example 1 as the test rod.

Animals were sacrificed at 2 weeks for outcome assessments consisting of faxitron radiographs and histomorphometry. Radiographs and histology of the 2 week distal femur explants indicated an overall increased bony callus formation in the rhBMP-2 treated side compared to placebo. In particular, higher CMC containing rods (B) formed medium to large bony calluses compared to lower CMC containing rods (A) which formed small to medium size calluses. Radiographs and histology of the subcutaneous implants also indicated bone formation in the rhBMP-2 treated side compared to placebo. In particular, higher CMC containing rods (B) formed a more robust ectopic bone response compared to lower CMC containing rods (A). Good biocompatibility was observed in all groups with no inflammatory response to the implants.

Example 4

Rabbit Intraosseous Local Biodistribution Study

Figure 2:
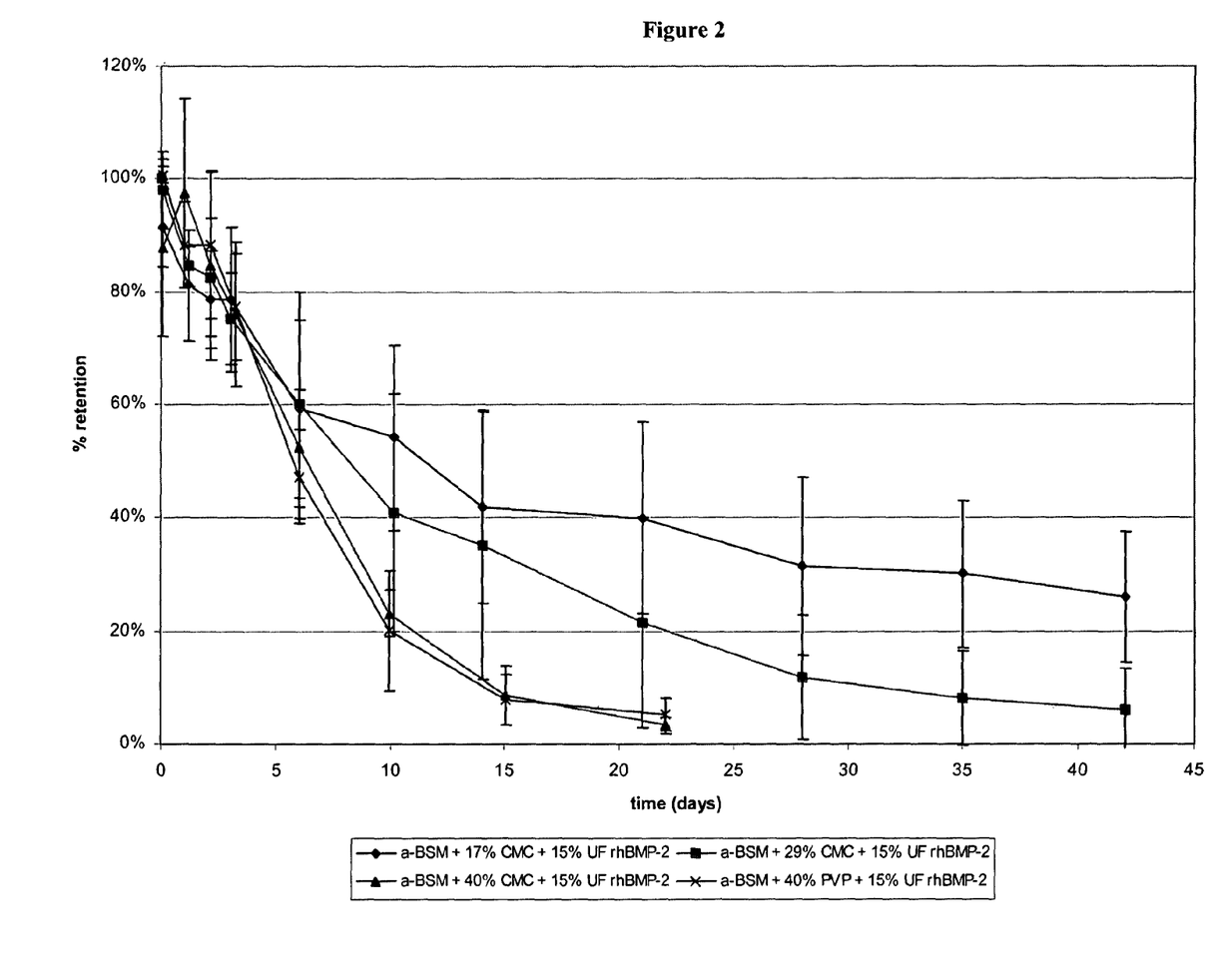
FIG. 2 is a graph showing the in vivo local retention of rhBMP-2 from α-BSM rods using 125I-rhBMP-2 as a tracer.

Rods A-D from Example 1 were injected percutaneously into rabbit distal femur intraosseous spaces (n=4 sites per group) using a 14-gauge catheter with a 16-gauge needle). In particular, 10 mm rods A-D containing approximately µCi 125I-rhBMP-2 were employed. The amount of radioactivity in the synthetic rods was measured before injection using a Capintec dose calibrator. Local rhBMP-2 retention was monitored over 4 weeks using gamma scintigraphy. Local in-vivo biodistribution data suggested a sustained release of rhBMP-2 from the rods and that higher % additive containing rods exhibited a faster in vivo release than their lower % additive counterparts as shown in FIG. 2.

Example 5

Formulation

Hardenable pastes containing either 1 mg rhBMP-2 per mL of paste or 4.5 mg rhBMP-2 per mL of paste were formulated by adding 2 mL of appropriately concentrated solutions of rhBMP-2 in the glycine-based aqueous buffer of Example 1 to 2.5 g α-BSM. The mixtures were kneaded in sterile bulbs for 1 minute to form hardenable paste.

Example 6

Cynomologous Monkey—Intraosseous Injection of Paste

The 1 mg per mL and 4.5 mg per mL hardenable pastes of Example 5 were extracted from the sterile bulbs using a 3 mL syringe fitted with an 18-gauge needle and then injected under fluoroscopic control into various intraosseous sites of cynomologous monkeys. Sites included distal femur, proximal femur, distal radius, proximal tibia. After 1 month, significant new bone was observed at the local sites where the rhBMP-2 was injected.

While the invention has been described in terms of preferred embodiments and specific examples, those skilled in the art will recognize through routine experimentation that various changes and modifications can be made without departing from the spirit and scope of the invention. Thus, the invention should be understood as not being limited by the foregoing detailed description, but as being defined by the appended claims and their equivalents.

What is claimed is:

1. A composition for injectable delivery of osteogenic proteins comprising an osteogenic protein and a poorly crystalline apatitic calcium phosphate, wherein the composition is in the form of a solid rod suitable for intraosseous injection in solid state, and wherein the osteogenic protein is present in an amount ranging from about 15% to about 40% by weight of the composition.

2. The composition of claim 1, wherein the osteogenic protein is selected from the group consisting of members of the bone morphogenetic protein family.

3. The composition of claim 2, wherein the osteogenic protein is selected from the group consisting of BMP 2, BMP 4, BMP 5, BMP 6, BMP 7, BMP 10, BMP 12 and BMP 13.

4. The composition of claim 3, wherein the osteogenic protein is BMP 2.

5. A method for preparing a composition of claim 1 comprising the steps of:
  (a) mixing a dry form of the osteogenic protein with a dry form of the poorly crystalline apatitic calcium phosphate to produce a dry mixture;
  (b) reconstituting the dry mixture by adding an aqueous buffer to form a paste;
  (c) molding the paste to form a rod shaped composition; and
  (d) drying the rod shaped composition of step (c) to form a rod-shaped composition for injectable delivery of osteogenic proteins,
wherein the osteogenic protein is present in an amount ranging from about 15% to about 40% by weight of the composition.

6. The method of claim 5, wherein the osteogenic protein is selected from the group consisting of members of the bone morphogenetic protein family.

7. The method of claim 6, wherein the osteogenic protein is selected from the group consisting of BMP 2, BMP 4, BMP 5, BMP 6, BMP 7, BMP 10, BMP 12 and BMP 13.

8. The method of claim 7, wherein the osteogenic protein is BMP 2.

9. The method of claim 5, wherein the aqueous buffer is selected from the group consisting of phosphate-buffered saline, saline, glycine-based buffers and combinations thereof.

10. The method of claim 5, wherein the ratio of aqueous buffer to dry mixture ranges from about 0.5:1 to about 2:1.

11. The method of claim 5, wherein the molding is accomplished using a method selected from the group consisting of molding, extruding, pressing, boring and combinations thereof.

12. The method of claim 5, further comprising a step of cutting the rod-shaped composition before or after step (d).

13. The method of claim 5, wherein the length of said rod-shaped composition is between about 1.0 mm and 5.0 cm.

14. A method of treating a mammal having a bone defect comprising administering to the site of the bone defect an amount of the composition for injectable delivery of osteogenic proteins of claim 1, wherein the amount is effective to treat the bone defect.

15. The method of claim 14, wherein the bone defect is osteoporotic bone.

16. A method of treating a mammal having a bone defect comprising the steps of:
(a) administering to the site of the bone defect an amount of the composition for injectable delivery of osteogenic proteins of claim 6, wherein the amount is effective to treat the bone defect; and
(b) administering to the site of the bone defect an effective amount of a bone resorption inhibitor.

17. The method of claim 16, wherein step (a) is performed prior to step (b).

18. The method of claim 16, wherein step (b) is performed prior to step (a).

19. The method of claim 16, wherein step (a) and step (b) are performed simultaneously.

20. A composition for injectable delivery of osteogenic proteins comprising an osteogenic protein and a poorly crystalline apatitic calcium phosphate, wherein the composition is in the form of a solid rod suitable for intraosseous injection in solid state, further comprising a bone resorption inhibitor.

21. The composition of claim 20, wherein the bone resorption inhibitor is a bisphosphonate.

22. The composition of claim 21, wherein the bisphosphonate is selected from the group consisting of alendronate, cimadronate, clodronate, EB 1053, etidronates, ibandronate, neridronate, olpadronate, pamidronate, risedronate, tiludronate, YH 529, and zoledronate.

23. A method for preparing a composition of claim 20 comprising the steps of:
(a) mixing a dry form of the osteogenic protein with a dry form of the poorly crystalline apatitic calcium phosphate to produce a dry mixture;
(b) reconstituting the dry mixture by adding an aqueous buffer to form a paste;
(c) molding the paste to form a rod shaped composition; and
(d) drying the rod shaped composition of step (c) to form a rod-shaped composition for injectable delivery of osteogenic proteins,
wherein the composition further comprises a bone resorption inhibitor and wherein a dry form of the bone resorption inhibitor is mixed in the dry mixture.

24. The method of claim 23, wherein the bone resorption inhibitor is a bisphosphonate.

25. The method of claim 24, wherein the bisphosphonate is selected from the group consisting of alendronate, cimadronate, clodronate, EB 1053, etidronates, ibandronate, neridronate, olpadronate, pamidronate, risedronate, tiludronate, YH 529, and zoledronate.

26. A method of treating a mammal having a bone defect comprising administering to the site of the bone defect an amount of the composition for injectable delivery of osteogenic proteins of claim 20, wherein the amount is effective to treat the bone defect.

27. A composition for injectable delivery of osteogenic proteins comprising an osteogenic protein and a poorly crystalline apatitic calcium phosphate, wherein the composition is in the form of a solid rod suitable for intraosseous injection in solid state, further comprising an additive selected from the group consisting of carboxymethylcellulose, hydroxypropylmethylcellulose, methylcellulose, polylactide, polyethylene glycol, polyvinylpyrrolidone, polyoxyethylene oxide, carboxyvinyl polymer, polyvinyl alcohol, dextran sulfate and combinations thereof.

28. The composition of claim 27, wherein the additive is present in an amount ranging from about 1% to about 90% by weight of the composition.

29. The composition of claim 28, wherein the additive is present in an amount ranging from about 20% to about 40% by weight of the composition.

* * * * *